(12) United States Patent
Goldfarb et al.

(10) Patent No.: US 10,925,754 B2
(45) Date of Patent: Feb. 23, 2021

(54) LINEAR ACTUATOR FOR ASYMMETRIC POWER GENERATION AND DISSIPATION

(71) Applicant: VANDERBILT UNIVERSITY, Nashville, TN (US)

(72) Inventors: Michael Goldfarb, Nashville, TN (US); Harrison Bartlett, Nashville, TN (US); Brian Lawson, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 16/475,332

(22) PCT Filed: Jan. 16, 2018

(86) PCT No.: PCT/US2018/013786
§ 371 (c)(1),
(2) Date: Jul. 1, 2019

(87) PCT Pub. No.: WO2018/132806
PCT Pub. Date: Jul. 19, 2018

(65) Prior Publication Data
US 2019/0336309 A1 Nov. 7, 2019

Related U.S. Application Data

(60) Provisional application No. 62/446,126, filed on Jan. 13, 2017.

(51) Int. Cl.
*F15B 1/02* (2006.01)
*A61F 2/68* (2006.01)
(Continued)

(52) U.S. Cl.
CPC .............. *A61F 2/68* (2013.01); *A61F 2/6607* (2013.01); *A61F 2/70* (2013.01); *F15B 1/02* (2013.01);
(Continued)

(58) Field of Classification Search
CPC .. A61F 2/64; A61F 2/66; F15B 15/088; F15B 2211/212; F15B 2211/40515; F15B 2211/426; F15B 7/00; F01B 3/10
See application file for complete search history.

(56) References Cited

U.S. PATENT DOCUMENTS 4,546,298 A * 10/1985 Wickham .............. B60T 8/1893
188/162
6,240,797 B1 * 6/2001 Morishima ......... F16H 25/2454
188/134
(Continued)

OTHER PUBLICATIONS

Written Opinion of the International Searching Authority for International Application No. PCT/US2018/013786 dated May 8, 2018.

*Primary Examiner* — Thomas E Lazo
(74) *Attorney, Agent, or Firm* — Nixon Peabody LLP

(57) ABSTRACT

An asymmetric linear actuator is provided which integrates a hydraulic dissipater and an electric motor and power screw which generates small forces. The actuator is configured so that an electric motor drives a power screw which drives a rod through a cylinder to provide linear actuation. The cylinder is fluid-filled and incorporates a piston that separates the cylinder into a first and second fluid chamber which are filled with a first and second volume of working fluid. Movement of the piston and rod assembly results in fluid movement between the first and second volumes of working fluid and through the fluidic restriction. The fluidic restriction can be proportionally controllable via an electric motor which enables controllable power dissipation via control of the fluidic restriction motor and controllable power generation via control of the power screw motor.

12 Claims, 7 Drawing Sheets

(51) Int. Cl.
*A61F 2/66* (2006.01)
*A61F 2/70* (2006.01)
*F15B 11/10* (2006.01)
*F15B 15/08* (2006.01)
*F15B 15/14* (2006.01)
*F15B 15/20* (2006.01)
*F16H 25/20* (2006.01)
*A61F 2/74* (2006.01)

(52) U.S. Cl.
CPC ............ *F15B 11/10* (2013.01); *F15B 15/088* (2013.01); *F15B 15/14* (2013.01); *F15B 15/20* (2013.01); *F16H 25/20* (2013.01); *A61F 2002/741* (2013.01); *A61F 2002/745* (2013.01); *A61F 2002/748* (2013.01); *F15B 2015/1495* (2013.01); *F15B 2015/206* (2013.01); *F15B 2211/212* (2013.01); *F15B 2211/40515* (2013.01); *F15B 2211/426* (2013.01)

(56) References Cited

U.S. PATENT DOCUMENTS

| | | | |
|---|---|---|---|
| 7,397,209 B2 * | 7/2008 | Hirai | B64C 13/42 318/280 |
| 7,531,006 B2 * | 5/2009 | Clausen | A61F 2/66 623/24 |
| 8,500,823 B2 | 8/2013 | Herr et al. | |
| 9,561,118 B2 * | 2/2017 | Clausen | A61F 2/66 |
| 2007/0194738 A1 | 8/2007 | Hirai | |
| 2013/0247700 A1 | 9/2013 | Mochizuki et al. | |
| 2014/0324190 A1 * | 10/2014 | Jonsson | A61F 2/66 623/24 |
| 2015/0265427 A1 | 9/2015 | Herr et al. | |
| 2015/0297364 A1 | 10/2015 | Goldfarb | |
| 2016/0001621 A1 | 1/2016 | Kato | |

* cited by examiner

200

200

200

200

300

400

LINEAR ACTUATOR FOR ASYMMETRIC POWER GENERATION AND DISSIPATION

CROSS-REFERENCE TO RELATED APPLICATIONS

This application is a National Phase of International Application No.: PCT/US2018/013786, filed Jan. 16, 2018, which claims priority to and the benefit of U.S. Provisional Patent Application No. 62/446,126, entitled "Linear Actuator for Asymmetric Power Generation and Dissipation" and filed Jan. 13, 2017, the content of which is hereby incorporated by reference in its entirety as if fully set forth herein.

FIELD OF THE INVENTION

The present invention relates to actuators, and more specifically to apparatus and methods for actuators with asymmetric power generation and dissipation.

BACKGROUND

Force actuators are ubiquitous in many modern devices. Force actuators include a first and second point of attachment, which are connected respectively to a first and second member of an external apparatus. Actuators provide a controllable force between the first and second member, where the second member moves relative to the first. A backdrivable force actuator can provide power generation when exerting a force in the direction of motion, and power dissipation when exerting a force in opposition to motion.

Conventional actuators are typically symmetric with regard to their capability to generate or dissipate power. For example, a DC permanent magnet electric motor generates and dissipates similar amounts of maximum power and does so while imposing similar magnitudes of maximum torque. Although some applications involving backdrivable force actuators require symmetric power and torque generation and dissipation properties, other applications are characterized by highly asymmetric power generation and dissipation requirements. In particular, some applications require controllable dissipation of large amounts of power at high force magnitudes while requiring controllable generation of relatively small amounts of power at low force magnitudes. Such applications may also require locking at high force magnitudes. If a standard power-symmetric actuator were to be used in such applications, the size of the actuator would be determined by the large power dissipation requirements, in which case the actuator would be both large and heavy relative to the power generation requirements.

In view of the foregoing, there is a need for a power-asymmetric actuator which can dissipate large amounts of power at high force magnitudes and generate relatively small amounts of power at low force magnitudes. The actuator should be compact and low-weight, and can also benefit from the ability to lock at high force magnitudes.

SUMMARY

Embodiments of the invention concern systems and methods for asymmetrically generating and dissipating power with a force actuator.

In a first embodiment of the invention, there is provided an actuator that includes an actuator body and piston assembly. In the actuator body, a cylinder bore is enclosed by a first cylinder end and a second cylinder end.

In the piston assembly, there is a piston, a piston rod, and a piston rod end. The piston is located at a first piston assembly end and slides linearly within the cylinder bore. The piston rod end is located at the second piston assembly end which is outside of the actuator body. This piston rod extends through the second end of the cylinder to the piston rod end. The piston has a first piston side and a second piston side. The first side faces the first cylinder end and the second piston side faces the second cylinder end.

The actuator has a first and second attachment point. The first attachment point is affixed to the actuator body; the second attachment point is affixed to the piston rod end.

The actuator has a power screw assembly. The power screw assembly has a power screw and a power screw nut. The power screw is contained within the piston rod and connected to the first cylinder end to allow rotation but prevent translation. The power screw nut is affixed to the piston assembly.

The actuator includes a first rotary motor affixed to the actuator body. The shaft of this motor drives the power screw assembly.

The actuator includes a first volume of working fluid and a second volume of working fluid. The first volume is contained within a space between the first end of the cylinder and the first side of the piston. The second volume is contained within a space between the second side of the piston and the second end of the cylinder.

In a second embodiment, the power screw is configured such that sliding of the piston assembly causes rotation of the power screw and first motor.

In another embodiment, the actuator has a first fluid port and a second fluid port. The first fluid port allows fluid to enter or leave the first volume. The second fluid port allows fluid to enter or leave the second volume. The first and second fluid ports can be connected via a fluidic restriction. The fluidic restriction can be an adjustable fluidic restriction controlled by a second motor, or controlled by an electrically controllable rheological change in the fluid. The actuator can also have a hydraulic accumulator which is in fluid communication with either the first or second volume of fluid.

In another embodiment, the actuator can have a first, second, and third control state. The first control state controls the actuator force during power generation. The second control state controls the actuator force during power dissipation. The third control state can de-energize the first motor and use the second motor to configure the adjustable fluidic restriction in a maximum restriction state. The actuator control state can be selected by a supervisory control scheme.

In another embodiment, the first and second attachment points of the actuator can be connected between first and second leg members of an ankle prosthesis.

In another embodiment, the first and second attachment points of the actuator can be connected between first and second leg members of a knee prosthesis.

DETAILED DESCRIPTION

Figure 1:
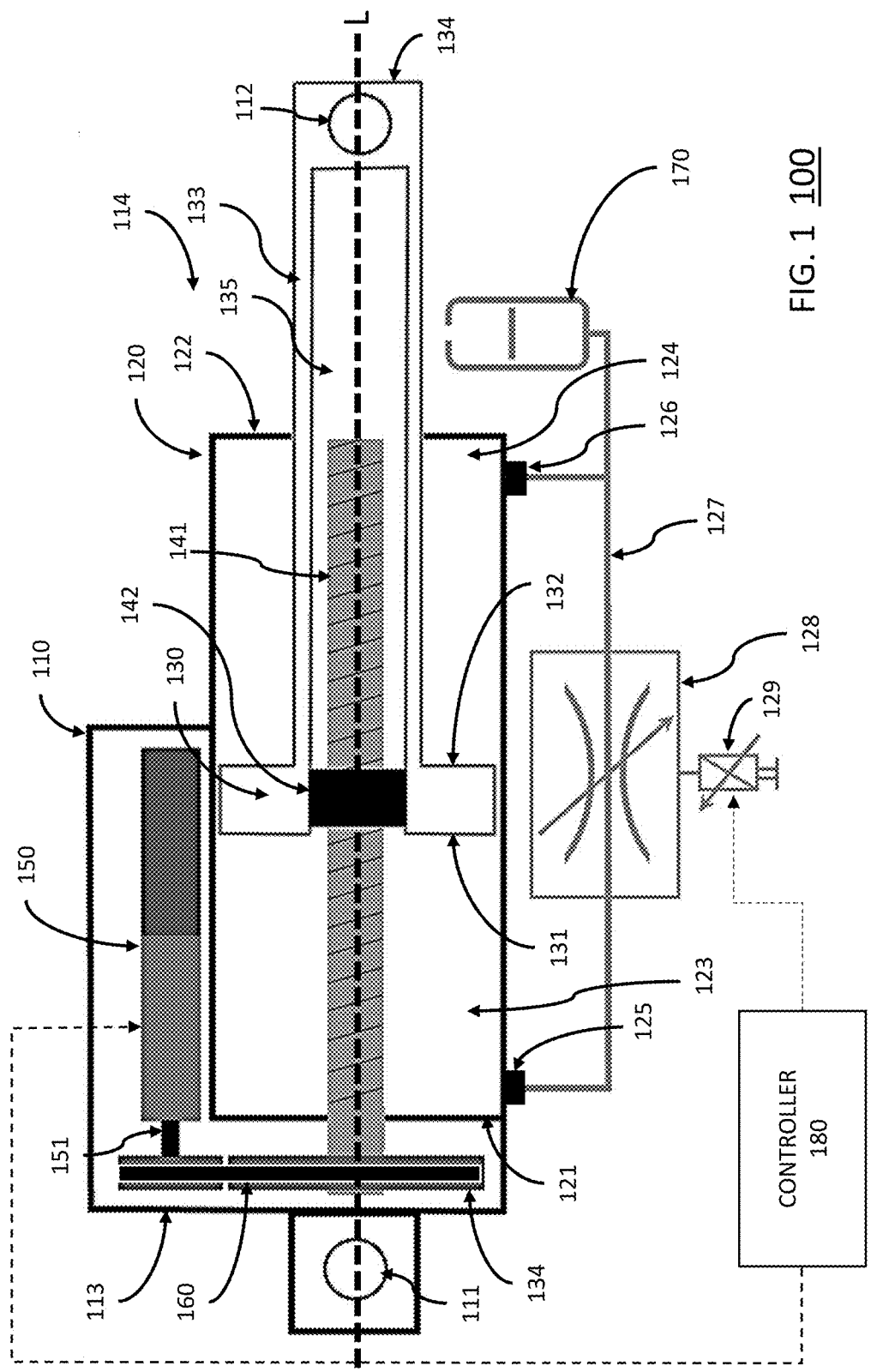
FIG. 1 schematically shows an asymmetric linear actuator according to an embodiment.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments are directed to a force actuator that is well-suited to applications requiring highly asymmetric power dissipation and generation. Specifically, the various embodiments are directed to systems and methods related to an actuator that provides high power dissipation at high forces, locking at high forces, and small amounts of power generation at relatively low forces. In particular, the various embodiments combine the characteristics of controllable hydraulic dissipation for high power dissipation with an electric motor and transmission for low power generation.

Force actuators according to the various embodiments leverage the fact that hydraulic cylinders, when combined with a proportionally controllable valve, can provide controllable power dissipation with a much higher force-to-weight ratio than a typical electric motor. Using a hydraulic cylinder for power delivery, however, requires an additional pressure source. Often, a motor and pump are used to generate hydraulic power, resulting in substantially lower efficiencies relative to using a motor to generate mechanical power directly. Accordingly, in the various embodiments, power delivery is provided by incorporating an electric motor and transmission to generate mechanical power for the cylinder.

In some embodiments, the force actuators can also be configured to provide a high-force locking capability in which power is neither dissipated nor generated. Such locking can be provided by a hydraulic dissipater if the system is constructed with fluid seals and a valve capable of maintaining fluid isolation.

To accomplish the foregoing, the various embodiments provide force actuators where an electric motor drives a power screw which drives a rod through a cylinder to provide linear motion. However, unlike contemporary linear actuators, the cylinders in the various embodiments are fluid-filled cylinders. Such a cylinder incorporates a piston that separates the cylinder into a first and a second fluid chamber which are filled respectively with a first and a second volume of working fluid.

Master cylinder type conventional actuators contain a first motor that drives a piston in a cylinder which may have a first and second volume of working fluid. Such an electrically-actuated master cylinder, however, lacks a piston rod that extends outside of the cylinder body. Therefore, the conventional master cylinder does not include a first and second point of attachment, which are necessary for a force actuator to exert a controllable force between a first and second member. Additionally, such a device is not characterized by two distinct mechanisms for force control, based on power asymmetry, as described here. That is, such a device does not employ a second motor to control a fluidic restriction. The conventional device additionally does not employ a control method that selects either the first or second motor, depending on the direction of power flow, to effect control of actuator force, as subsequently described.

In the force actuator described herein, the first and second volumes of working fluid are in fluid communication through a fluidic restriction system, such that movement of the piston and rod assembly results in fluid movement between the first and second volumes of working fluid and through the fluidic restriction. In some embodiments, the fluidic restriction is within the piston, cylinder, or piston-cylinder interface. In some embodiments, the fluidic restriction is proportionally controllable via a motor or other adjusting device, which enables controllable power dissipation via control of the adjustable fluidic restriction and controllable power generation via control of the power-screw motor. The fluid system can also include an accumulator to account for volume changes in the hydraulic subsystem. As such, actuators according to the various embodiments can include two motors—a first motor for providing low-force power generation through the power screw, and a second motor for providing high-force power dissipation or locking through the valve.

In view of the foregoing, the various embodiments can be considered as means to provide a power-asymmetric force actuator (PAFA). A PAFA is intended for power-asymmetric applications such as those characterized by relatively high magnitudes of force and power during power dissipation and relatively low magnitudes of force and power during power generation. Since the force and power density of hydraulic actuation is substantially greater than the force and power density of the electromagnetic actuation, the PAFA is able to provide substantially greater force and power in dissipation than in generation.

One application that would benefit from a PAFA is a prosthetic ankle. Although an ankle joint transmits torque rather than force, a force actuator is commonly configured between two rotationally coupled members to provide a torque between them. In a prosthetic ankle, the joint may provide a locking function during the stance phase of gait, which requires large torque capacity in the joint. The ankle joint may additionally benefit from a dissipative function, such as that required during the early stance phase of gait when descending stairs, which requires the dissipation of large amounts of power at relatively high values of torque. Finally, the ankle may further benefit from the ability to generate relatively small amounts of power, such as that required to dorsiflex the ankle joint during the swing phase of walking or to plantarflex the ankle joint in the swing phase of stair descent.

Another application that would benefit from a PAFA is a prosthetic knee joint. A prosthetic knee joint should provide high-torque resistance or locking to prevent knee buckling in the stance phase of walking. Prosthetic knee joints also should provide high-torque and high-power dissipation to provide stance-knee yielding when walking down stairs or down slopes. Lastly, prosthetic knee joints can benefit from low-torque power generation to assist with the swing phase of walking and other activities. In the cases of both the prosthetic ankle and knee applications, providing these functions in a compact and low-weight package is among the highest of design priorities.

FIG. 1 shows a schematic of PAFA 100 according to an embodiment. As shown in FIG. 1, PAFA 100 which includes an actuator body 110, a first attachment point for the actuator body 111, a second attachment point for the actuator body 112, a first end of the actuator body 113, a second end of the actuator body 114, a cylinder bore 120, a first end of the cylinder 121, a second end of the cylinder 122, a first fluid volume 123, a second fluid volume 124, a first fluid port 125, a second fluid port 126, an external flow path 127, an adjustable fluidic restriction 128, a fluid restriction motor 129, a piston 130, a first piston side 131, a second piston side 132, a piston rod 133, a piston rod end 134, a power screw 141, a power screw nut 142, a first rotary motor 150, a motor shaft 151, a rotary transmission 160, and a hydraulic accumulator 170. Each of these elements will be described below in greater detail.

Although FIG. 1 illustrates PAFA 100 with certain enumerated components, this is solely for ease of illustration. In the various embodiments, a PAFA can include more or less components than illustrated in FIG. 1. Further, some or all these components may be implemented in a variety of ways not illustrated in FIG. 1

As noted above, PAFA 100 includes an actuator body 110. The actuator body 110 includes a hydraulic fluid filled cylinder defined by a cylinder bore 120 that is enclosed by a first cylinder end 121 and second cylinder end 122. The PAFA 100 further includes a piston assembly, which is comprised of a piston 130 that slides linearly through the cylinder bore 120 along a longitudinal axis L, a piston rod 133 that slides through and extends from the second cylinder end 122 along axis L, and a piston rod end 134 that is located outside of the actuator body 110. The piston 130 is comprised of a first piston side 131 and a second piston side 132, where the first side 131 faces the first end of the cylinder 121 and the second piston side 132 faces the second end of the cylinder 122.

The PAFA 100 further includes of first 111 and second 112 attachment points disposed along axis L, where the first attachment point 111 is affixed to the first end 113 of the actuator body 100, and the second attachment point 112 is disposed at the second end of the piston assembly 134. Thus, the PAFA 100 is configured to apply a controllable force between the first 111 and second 112 attachment points.

The PAFA 100 further includes a power screw assembly defined by a power screw 141 and power screw nut 142. The power screw 141 can be a lead screw, ball screw, roller screw, or other similar screw. The power screw 141 is rotationally affixed at or near the first cylinder end 121 and extends along axis L. The power screw nut 142 is disposed in the piston assembly along axis L. The piston rod 133 is configured to include a space or volume 135 to encompass the power screw 141. In operation, the rotation of the power screw 141 drives the piston assembly along the length of the cylinder bore 120. Conversely, movement of the piston assembly along the length of the cylinder bore 120 drives the power screw 141 in rotation.

The PAFA 100 further includes a first rotary motor 150. As shown in FIG. 1, the housing of the rotary motor 150 can be mounted the actuator body 110. The motor 150 can include a shaft 151 that is configured to drive the power screw 141 and hence move the piston assembly. Driving the piston assembly with the power screw 141 requires that the piston assembly include a feature that prevents rotation of the piston 130 assembly relative to the actuator body 110. Such a feature may be implemented within the cylinder. Alternatively, an external constraint through the first 111 and second 112 attachment points can provide such a feature.

The rotary motor 150 can drive the power screw 141 directly or through a transmission element 160. Thus, the rotary motor 150 may be arranged coaxially with the power screw 141, or along another axis and connected through rotary transmission elements 160. In the implementation of FIG. 1, motor 150 is arranged in parallel with the power screw 141, and the motor shaft 151 is rotationally affixed to the power screw 141 through a rotary transmission 160. Rotary transmissions can be constructed of gears, belts, chains or similar mechanical elements.

The PAFA 100 further includes a first fluid volume 123 and a second fluid volume 124 defined in the cylinder bore 120. The first fluid volume 123 is contained within a space between the first side of the piston 131 and the first end of the cylinder 121. The second fluid volume 124 is contained within a space between the second side of the piston 132 and the second end of the cylinder 122. In certain embodiments, the volume 135 within the piston rod 133 can be in fluid connection with either of the first 123 or the second 124 fluid volumes. Similarly, the volumes of actuator body 110 that encompasses the first motor 150 and/or the transmission 160, can also be in fluid connection with either of the first 123 or the second 124 fluid volumes.

The PAFA 100 further includes a first fluid port 125 and a second fluid port 126. In some embodiments, these fluid ports can be located in the piston. In another embodiment, the first fluid port 125 provides fluid communication between the first fluid volume 123 and an external flow path 127, while the second fluid port 126 provides fluid communication between the second fluid volume 124 and the external flow path 127. The first 125 and second 126 fluid ports are configured to be in fluid connection through a fluidic restriction 128, where the fluidic restriction 128 is an adjustable valve or opening that can vary the resistance to fluid flow. In certain embodiments, a second motor 129 can be used to modulate or otherwise adjust the fluidic restriction 128. In some embodiments, this second motor 129 can also be a rotary motor. In the various embodiments, the fluid restriction 128 can be any type of adjustable valve for regulating flow. In certain embodiments, the hydraulic valve 129 can be pressure-balanced.

The PAFA 100 can further include a hydraulic accumulator 170, which is in fluid communication with either the first 123 or second 124 volume of fluid. In the embodiment of FIG. 1, the hydraulic accumulator 170 is in fluid communication with the second volume of fluid 124.

The PAFA 100 is further configured to operate with a controller 180. In particular, the controller 180 is configured to generate control signals for first rotary motor 150 and second motor 129.

Control States

A PAFA in accordance with the various embodiments, such as PAFA 100, can be controlled through at least a first control state and a second control state. For example, as shown in FIG. 1, a controller 180 can be provided to configure the PAFA 100 in one of these controller states. The first control state corresponds to force control during power generation and the second control state corresponds to force control during power dissipation. In some embodiments, the first or second control state is selected via a supervisory control scheme. In other embodiments, the first or second control state can be selected as a function of the direction of the measured velocity between the first and second attachment points and the direction of the desired force. However, in the various embodiments, selection of the control state is not limited to any particular circumstances. Rather, the PAFA can be alternated between the different control states as needed. For ease of illustration, operation will be described with respect to PAFA 100 under the control of controller 180.

When the first control state is selected by controller 180, the controller 180 generates control signals for first motor 150 to exert the desired controllable force between the first 111 and second 112 attachment points. This can be done via established open-loop or feedback control techniques. Contemporaneously, the controller generates control signals for the second motor 129 to configure the fluidic restriction 128 for the minimum amount of resistance. For example, in the case of fluidic restriction 128 implemented as an adjustable valve, the control signals from controller 180 would configured to cause the adjustable value to have a maximum valve opening. In another embodiment, the controller can generate signals for the second motor 129 to configure the fluidic restriction 128 to provide a nominal amount of damping, which can provide additional stability margin and enhanced force control performance of first motor 150 when configured in a feedback control loop.

When the second control state is selected, the first motor 150 is de-energized. That is, the controller 180 provides no control signals for first motor 150. Contemporaneously, controller 180 generates control signals for the second motor 129 so as to adjust the resistance through fluidic restriction 128. The amount of resistance can be adjusted so as to provide a desired controllable force between the first and second attachment points via established open-loop or feedback control techniques.

In some embodiments, a third control state can be provided, which corresponds to a locked state. In the locked state, the piston assembly can be locked against either extension or retraction, depending on which side an accumulator is located. Referring back to FIG. 1, if the accumulator 170 is configured to be in fluid communication with the first fluid volume 123, the piston assembly can be locked against extension. If the accumulator 170 is configured to be in fluid communication with the second fluid volume 124, the piston assembly can be locked against retraction. In either case, when the PAFA 100 is configured in this control state, the first motor 150 is de-energized while the controller 180 generates control signals to cause the second motor 129 is configured to close the fluidic restriction 128 so that fluid is blocked from flowing through fluid restriction 128.

In another embodiment, the power generation subsystem can be controlled so as to modulate the behavior of the power dissipation subsystem. For example, in some applications, the nominal behavior of the PAFA is configured to be dissipative, using control of the second motor 129 to modulate the fluidic restriction to provide the desired control force. In such applications, the first motor can be used to further modulate the control force around the nominally dissipative behavior, or to provide a brief period of power generation around the nominally dissipative behavior. For example, in the case of a knee prosthesis, the swing-phase behavior may be nominally dissipative, in which case the force would be provided by control of the second motor; in the case of stumble, however, the first motor could be temporarily employed without reconfiguring the second motor to provide a brief period of power generation in response to the stumble perturbation. Similarly, in other applications involving nominally dissipative behavior, since the bandwidth and precision of force control through the power screw via the first motor is likely to be improved relative to the bandwidth and precision of force control of the fluidic system via the second motor, the first motor can be used to provide improved bandwidth and precision in modulating a nominally dissipative force. In such applications, the second motor is controlled to configure the fluidic restriction to provide a nominal control force, while the first motor is controlled to provide a relatively small-amplitude force modulation that is superimposed into the force provided by the second motor and fluidic restriction.

Figure 2A:
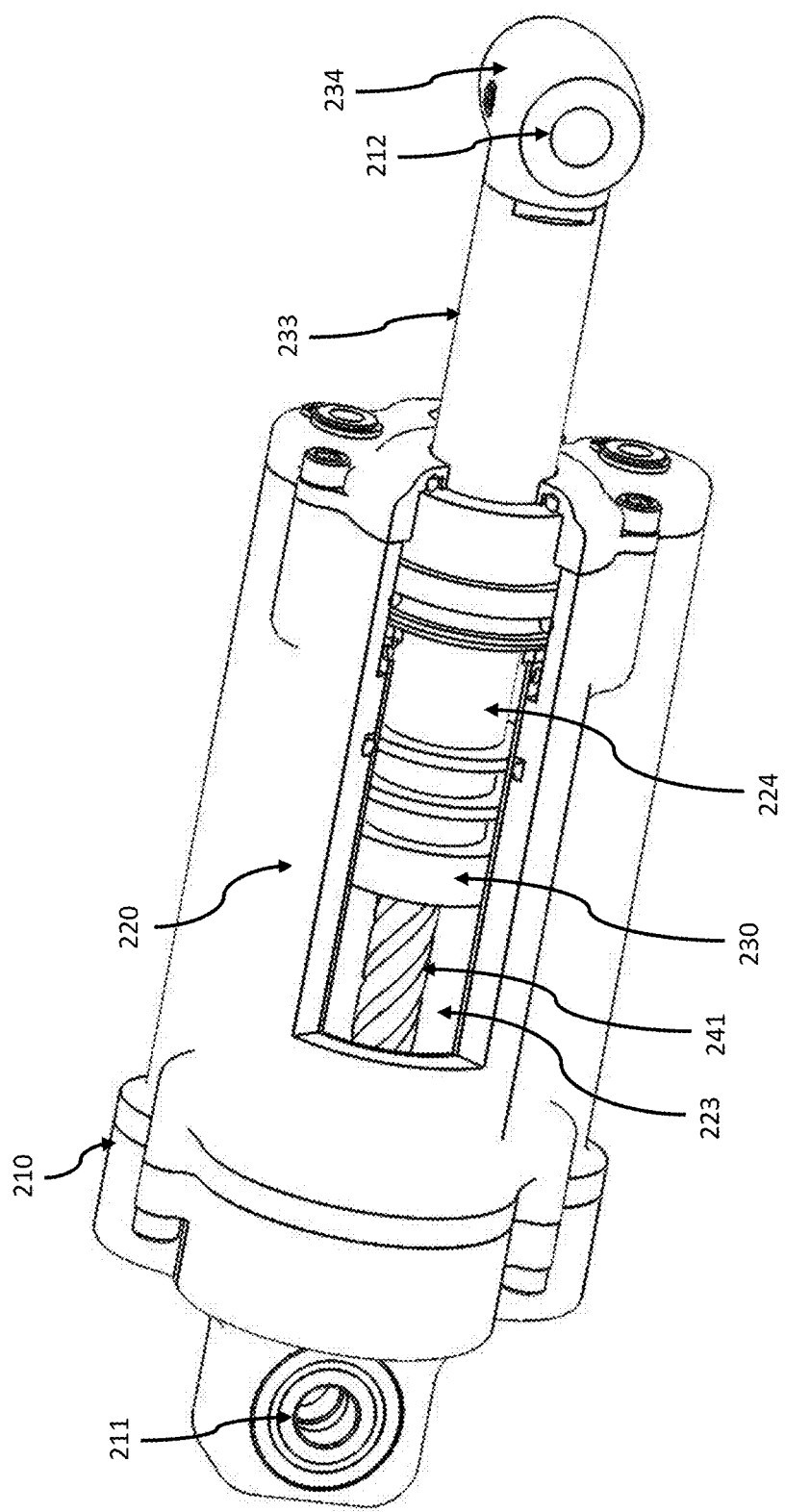
FIG. 2A is a partial cross-section view of an symmetric linear actuator according to an embodiment.
Figure 2B:
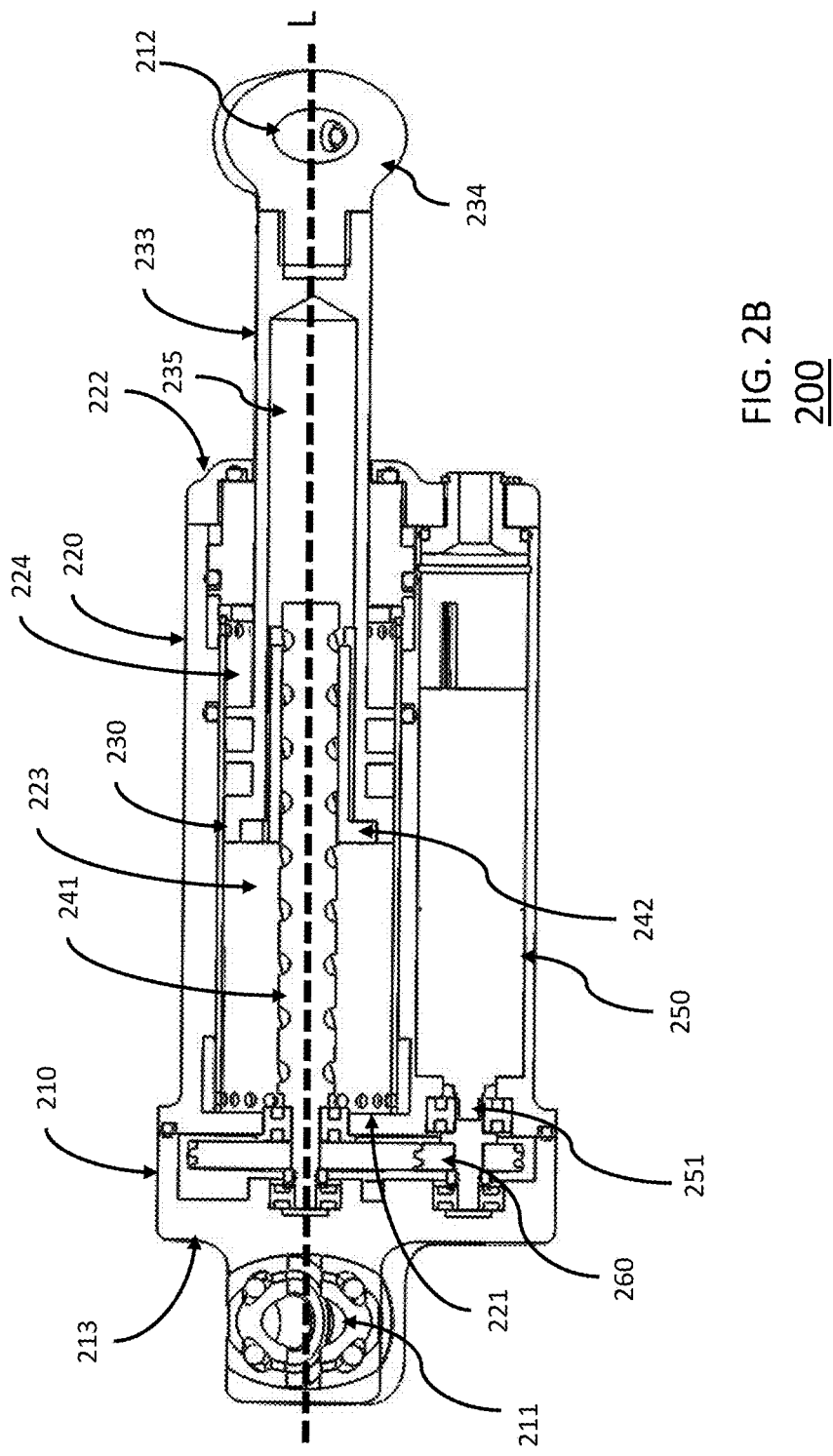
FIG. 2B is another cross-section view of the asymmetric linear actuator for FIG. 2A, showing the power generation subsystem.
Figure 2C:
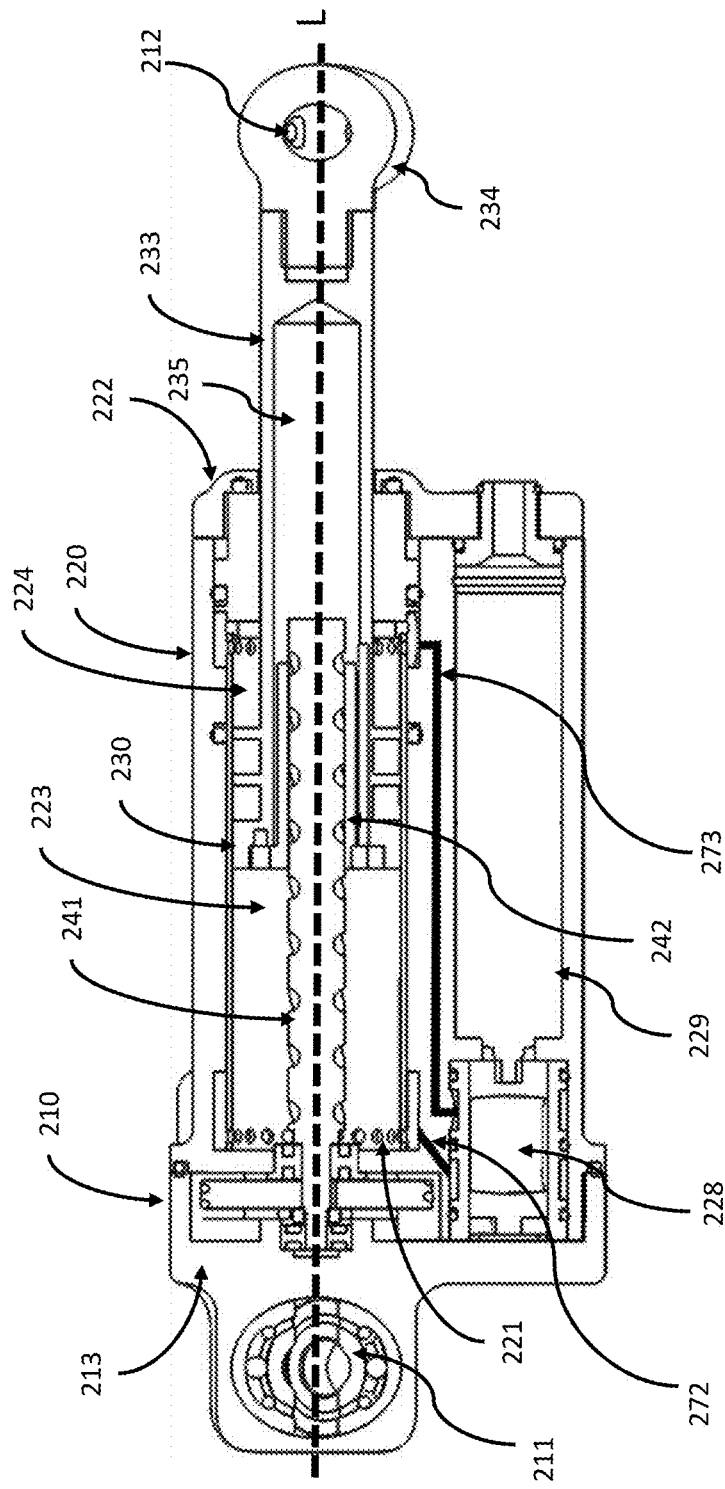
FIG. 2C is another cross-section view of the asymmetric linear actuator for FIG. 2A, showing the hydraulic subsystem.
Figure 2D:
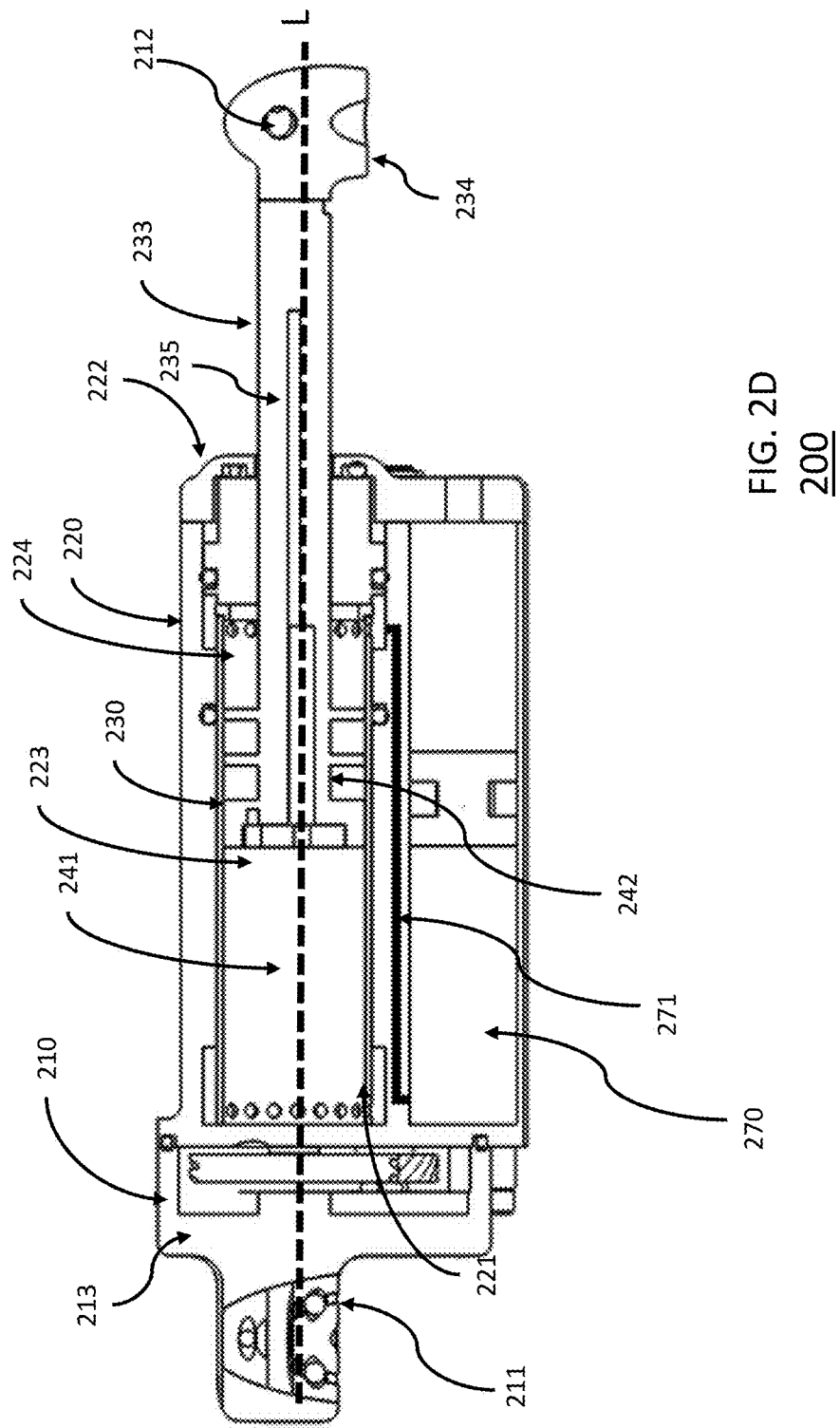
FIG. 2D is another cross-section view of the asymmetric linear actuator for FIG. 2A, showing the accumulator.

Now turning to FIGS. 2A, 2B, 2C, and 2D there is shown an exemplary implementation of a PAFA 200 in accordance with the various embodiments. FIG. 2A shows an isometric, partial cutaway view of PAFA 200. FIG. 2B shows a cross-section view of PAFA 200, where the power generation subsystem is shown. FIG. 2C shows another cross-section view of PAFA 200, where the power dissipation subsystem is shown. FIG. 2D shows a cross-section view of PAFA 200, where an accumulator is shown. As discussed above with respect to FIG. 1, in some implementations, the first motor 150 and the second motor 129 can be both rotary motors. FIGS. 2A, 2B, 2C, and 2D show such an implementation.

As shown in FIGS. 2A, 2B, 2C, and 2D PAFA 200 includes elements 210, 211, 212, 213, 220, 221, 222, 223, 224, 228, 229, 230, 233, 234, 235, 241. 242, 250, 251, 270, 271, and 273. These elements are comparable to elements 110, 111, 112, 113, 120, 121, 122, 123, 124, 128, 129, 130, 133, 134, 135, 141. 142, 150, 151, 170, 171, and 173 of PAFA 100. Accordingly, the description of these elements in FIG. 1 is sufficient for describing the comparable elements in PAFA 200, except where as noted below. Additionally, PAFA 200 includes an accumulator flow path 271, a first valve flow path 272 (between restriction or valve 228 and first fluid volume 223), and a second valve flow path 273 (between restriction 228 and second fluid volume 224). Further, PAFA 200 can be configured to operate with a controller (not shown) to allow the PAFA to alternate between the first, second, and (optionally) third control states, or in accordance with other control embodiments as discussed above.

Turning first to FIG. 2B, the power generation subsystem is shown for PAFA 200. Similar to that illustrated in FIG. 1, the power generation subsystem of PAFA 200 includes a first rotary motor 250. The motor 250 can include a shaft 251 that is configured to drive the power screw 241 and hence move the piston assembly defined by piston 230 and piston rod 230, and hence also established a controllable force between attachment points 211 and 212. In PAFA 200, the motor 250 drives the power screw 241 through a transmission element 260 and the motor 250 is arranged in parallel with the power screw 241.

Turning next to FIG. 2C. the power dissipation subsystem is shown for PAFA 200. Similar to that illustrated in FIG. 1, the power dissipation subsystem of PAFA 200 includes a first fluid volume 223 on one side of piston 230 and a second fluid volume 224 on the second side of piston 230. In this embodiment, the piston includes grooves for seals that isolate fluid in the first fluid volume from fluid in the second fluid volume. The first 223 and second 224 fluid volumes are fluid connected via fluid restriction 228, which is controlled by a second motor 229. The physical external flow path 227 cannot be seen in this section, since it exists in another sectional plane, so a schematic path is shown instead. In PAFA 200, the second motor 229 is also a rotary motor arranged in parallel with power screw 241 and parallel with first rotary motor 250. In this way, both the power generation and power dissipation subsystems can be integrated compactly into the actuator body 210, as shown in FIG. 2A. Although the first and second electric motors 229 and 250 are of similar size, the PAFA is about to provide forces and power associated with power dissipation one to two orders of magnitude greater than the corresponding forces and power associated with power generation. FIG. 2C shows the valve flow path 273 which connects the valve 272 to the cylinder.

FIG. 2D shows the accumulator fluid path 271 for PAFA 200. PAFA 200 can include an accumulator 270 which is in fluid connection with the first 223 or second 224 volume of fluid. The accumulator 270 allows for the change in fluid volume in cylinder bore 220 as the piston rod 233 is retracted into the actuator body. A schematic flow path between the accumulator and the second fluid volume 224 is shown.

Ankle Prosthesis

Figure 3:
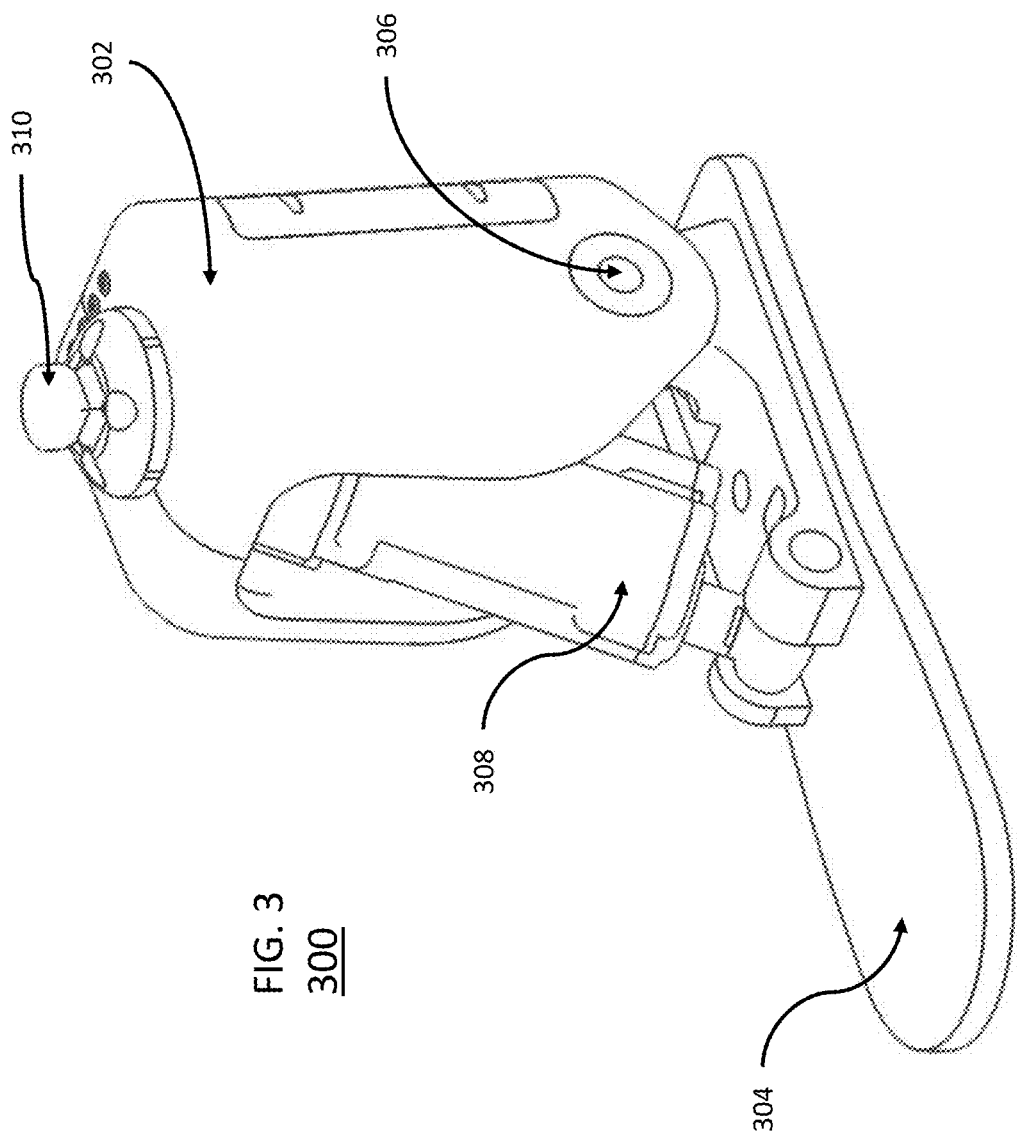
FIG. 3 shows an asymmetric linear actuator according to an embodiment of the invention mounted in a prosthetic ankle joint.

FIG. 3 shows an exemplary ankle prosthesis 300 which includes an asymmetric linear actuator according to an embodiment. The ankle prosthesis 300 includes a shank member 302 and a foot member 304, rotatably coupled to each other via ankle joint 306. The ankle prostheses 300 also includes a force actuator 308. The force actuator 308 is configured between the shank member 302 and the foot member 304. The force actuator 308 can be any of the PAFA configurations illustrated above or any other force actuator in accordance with the various embodiments. A controller (not shown) for the force actuator 308 can be disposed in ankle prosthesis 300 or elsewhere. The ankle prosthesis 300 can also include attachment point 310 for a socket interface to a residual limb or for connection to a knee prosthesis.

In operation, the force actuator 308 (via an associated controller) can be configured to provide a locking function during a stance phase of the gait. The force actuator 308 can also be configured (via an associated controller) to provide a dissipative function for large amounts of power at relatively high values of torque, such as that required when descending stairs. Lastly, the force actuator 308 can also be configured (via an associated controller) to generate relatively small amounts of power, such as that required to dorsiflex the ankle joint during the swing phase of walking or to plantarflex the ankle joint during the swing phase of stair descent.

In the configuration of FIG. 3, the structure of the ankle prosthesis 300 provides the external constraint needed to prevent rotation of the piston assembly of the force actuator 300. Therefore, an ankle prosthesis constructed according to the present disclosure would provide these functions in a compact and low-weight package.

Knee Prosthesis

A knee prosthesis can also be configured with an asymmetric linear actuator according to the various embodiment. The asymmetric linear actuator can be mounted between a first leg member (e.g., a thigh member) and a second leg member (e.g., a shank member) that are rotatably coupled via a joint, similar to the ankle prosthesis shown in FIG. 3.

Figure 4:
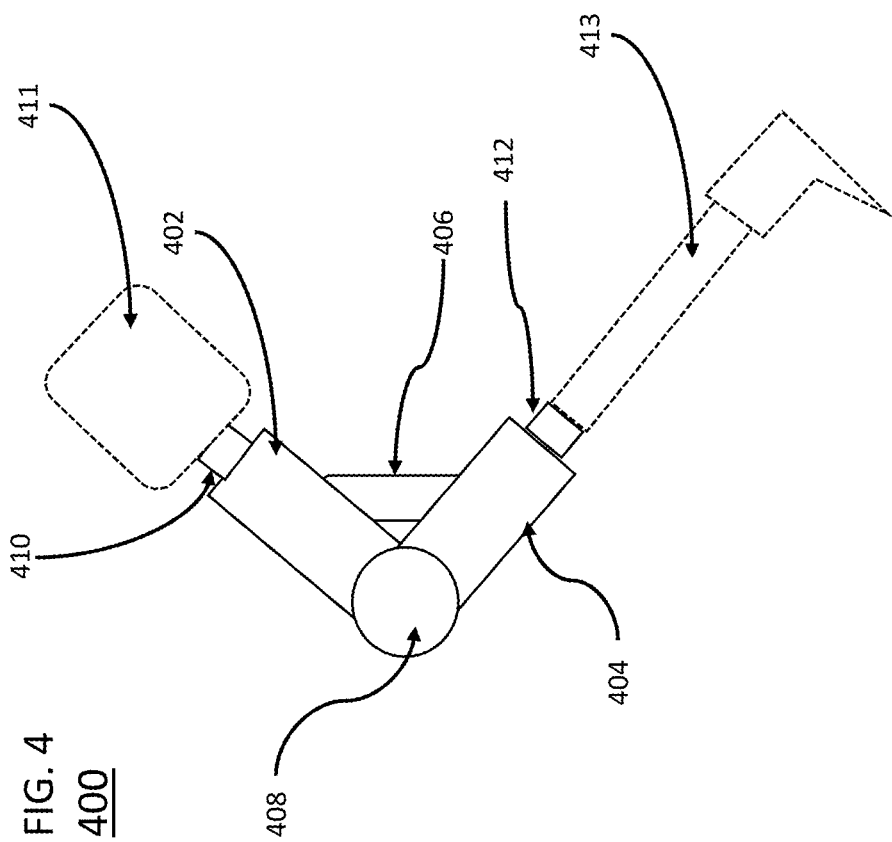
FIG. 4 shows an asymmetric linear actuator according to an embodiment of the invention mounted in a prosthetic knee joint.

FIG. 4 shows an exemplary knee prosthesis 400 which includes an asymmetric linear actuator according to an embodiment. The knee prosthesis 400 includes a shank member 404 and a thigh member 402, rotatably coupled to each other via a joint 408. The knee prostheses 400 also includes a force actuator 406. The force actuator 406 is configured between the shank member 404 and the thigh member 402. The force actuator 406 can be any of the PAFA configurations illustrated above or any other force actuator in accordance with the various embodiments. A controller (not shown) for the force actuator 406 can be disposed in knee prosthesis 400 or elsewhere. The knee prosthesis 400 can also include an attachment point 410 for attaching to a socket of a residual limb 411. Further, the knee prosthesis 400 can also include a second attachment point 412 for attaching a shank/foot member 413.

In operation of such a knee prosthesis, the force actuator can provide high-torque and high-power dissipation to provide stance-knee yielding when walking down stairs or down slopes. The knee prosthesis can also generate low-torque power to assist with the swing phase of walking and other activities. A knee prosthesis constructed according to the present disclosure would provide these functions in a compact and low-weight package.

Rotary Configuration

A PAFA can alternatively be embodied in a rotary configuration which would impose a controllable torque rather than a controllable force. In this embodiment, the hydraulic actuator can be a rotary actuator, such as a rotary vane actuator. In this rotary embodiment, the first attachment point is affixed to the actuator housing, and the second attachment point is affixed to the rotary shaft. The first motor can drive the rotary axis either directly or through a rotary transmission. Fluid can move from the first volume of fluid to the second volume of fluid either within the rotary actuator, or via an external flow path. The fluidic restriction can be located within the rotary actuator, or in the external flow path. The fluidic restriction can be controlled via a second motor, or by an electrically controllable rheological change in the fluid. A rotary PAFA may not require an accumulator, since it does not include a sliding piston rod.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. An actuator for exerting a controllable force between a first and second attachment point, comprising:
    an actuator body;
    a piston assembly;
    a power screw assembly connecting the actuator body to the piston assembly;
    wherein the actuator body includes a cylinder bore configured for holding a working fluid, the cylinder bore having a first cylinder end and second cylinder end, wherein the piston assembly includes a piston that slides linearly within the cylinder bore and a piston rod that extends from the piston through the second cylinder end to a piston rod end, which is located outside the actuator body, wherein the actuator body includes a first attachment point affixed to the actuator body and a second attachment point affixed to the piston rod end;
    wherein the power screw assembly comprises a power screw connected to the actuator body to allow rotation and prevent translation, a power screw nut affixed to the piston assembly, and a first rotary motor disposed in the actuator body and configured to drive the power screw assembly;
    wherein the piston assembly divides the cylinder bore into a first volume of the working fluid and a second volume of the working fluid,
    wherein sliding of the piston causes rotation of the power screw and first motor,
    wherein the actuator further comprises a first fluid port and a second fluid port, the first fluid port allowing fluid to enter or leave the first volume of the working fluid, the second fluid port allowing fluid to enter or leave the second volume of the working fluid, the first and second fluid ports being connected via a fluidic restriction, the fluidic restriction being an adjustable fluidic restriction controlled by a second motor,
    wherein the actuator further comprises a hydraulic accumulator in fluid communication with at least one of the first volume of working fluid and the second volume of working fluid,
    wherein the actuator further comprises at least one of a first control state and a second control state, the first control state controlling the actuator force during power generation and the second control state controlling the actuator force during power dissipation.

2. The actuator of claim 1, wherein in the first control state further comprises:
    the first motor exerting the desired actuator control force between the first and second actuator attachment points and where the second motor configuring the adjustable fluidic restriction in a minimum restriction state.

3. The actuator of claim 1, where in the second control state further comprises:
    the first motor being de-energized and the second motor being used to control the adjustable fluidic restriction to provide the desired actuator control force between the first and second actuator attachment points.

4. The actuator of claim 1, wherein the actuator further comprises:
    a third control state, wherein the first motor is de-energized and the second motor configures the adjustable fluidic restriction in a maximum restriction state.

5. The actuator of claim 1, wherein the actuator control state is selected via a supervisory control scheme.

6. The actuator of claim 1, configured within an ankle prosthesis, further comprising:
    a first leg member and second leg member, wherein the first and second leg members are rotationally coupled at the ankle joint and the first and second attachment points of the actuator are connected between the first and second leg members.

7. The actuator of claim 1, configured within a knee prosthesis, further comprising:
    a first leg member and second leg member, wherein the first and second leg members are rotationally coupled at the knee joint and the first and second attachment points of the actuator are connected between the first and second leg members.

8. An actuator for exerting a controllable force between a first and second attachment point, comprising:
    an actuator body;
    a piston assembly;
    a power screw assembly connecting the actuator body to the piston assembly;
    wherein the actuator body includes a cylinder bore configured for holding a working fluid, the cylinder bore having a first cylinder end and second cylinder end, wherein the piston assembly includes a piston that slides linearly within the cylinder bore and a piston rod that extends from the piston through the second cylinder end to a piston rod end, which is located outside the actuator body, wherein the actuator body includes a first attachment point affixed to the actuator body and a second attachment point affixed to the piston rod end;
    wherein the power screw assembly comprises a power screw connected to the actuator body to allow rotation and prevent translation, a power screw nut affixed to the piston assembly, and a first rotary motor disposed in the actuator body and configured to drive the power screw assembly;
    wherein the piston assembly divides the cylinder bore into a first volume of the working fluid and a second volume of the working fluid,
    wherein sliding of the piston causes rotation of the power screw and first motor,
    wherein the actuator further comprises a first fluid port and a second fluid port, the first fluid port allowing fluid to enter or leave the first volume of the working fluid, the second fluid port allowing fluid to enter or leave the second volume of the working fluid,
    wherein the actuator further comprises at least one of a first control state and a second control state, the first control state controlling the actuator force during power generation and the second control state controlling the actuator force during power dissipation.

9. The actuator of claim 8, where the first and second fluid ports are connected exclusively via at least one fluidic restriction.

10. The actuator of claim 8, wherein the actuator further comprises:
   a hydraulic accumulator in fluid communication with at least one of the first volume of working fluid and the second volume of working fluid.

11. The actuator of claim 8, configured within an ankle prosthesis, further comprising:
   a first leg member and second leg member, wherein the first and second leg members are rotationally coupled at the ankle joint and the first and second attachment points of the actuator are connected between the first and second leg members.

12. The actuator of claim 8, configured within a knee prosthesis, further comprising:
   a first leg member and second leg member, wherein the first and second leg members are rotationally coupled at the knee joint and the first and second attachment points of the actuator are connected between the first and second leg members.

\* \* \* \* \*